United States Patent [19]

Cerretti et al.

[11] Patent Number: 4,879,374
[45] Date of Patent: Nov. 7, 1989

[54] BOVINE INTERLEUKIN-1β DNA SEQUENCE

[75] Inventors: Douglas P. Cerretti; Brian S. Davis; Charles R. Maliszewski, all of Seattle, Wash.

[73] Assignee: Immunex Corporation, Seattle, Wash.

[21] Appl. No.: 25,462

[22] Filed: Mar. 13, 1987

[51] Int. Cl.[4] .......................................... C07H 19/073
[52] U.S. Cl. ....................................... 536/27; 536/28; 536/29
[58] Field of Search ............... 536/27, 28, 29; 435/68; 530/351

[56] References Cited

U.S. PATENT DOCUMENTS

| | | | |
|---|---|---|---|
| 4,404,280 | 9/1983 | Gillis | 435/68 |
| 4,406,830 | 9/1983 | Fabricius et al. | 530/351 |
| 4,681,844 | 7/1987 | Fabricius et al. | 435/68 |

OTHER PUBLICATIONS

Wingfield et al., J. of Chromatography, v. 387, pp. 291-300, 1987, Jan.
Mizel et al., J. of Immunology, v. 131, pp. 1834-1837, 1983.
Gray et al., J. of Immunology, v. 137, pp. 3644-3648, 1986, Dec.
Cameron et al., J. Exp. Med., v. 164, pp. 237-250, 1986, Jul.
Matsushima et al., Biochemistry, v. 25, pp. 3424-3429, 1986, Jun.
Clark et al., Nucleic Acids Res., v. 14(20), pp. 7897-7914, 1986, Oct.
Krakauer et al., Chem. Abstr., v. 102:219,322q, 1985.
Prestidge et al., Chem. Abstr., v. 102;77013p, 1985.
March et al., Nature, v. 315, pp. 641-647, 1985.
Oppenheim et al., "There is More Than One Interleukin 1", *Immunol. Today* 7:45 (1986).
Durum et al., "Interleukin 1: An Immunological Perspective", *Ann. Rev. Immunol.* 3:263 (1985).
March et al., "Cloning, Sequence and Expression of Two Distinct Human Interleukin-1 Complementary DNAs", *Nature* 315:641 (1985).
Gubler et al., "Recombinant Human Interleukin 1α: Purification and Biological Characterization", *J. Immunol.* 136:2492 (1986).
Tocci et al., "Expression in *Escherichia coli* of Fully Active Recombinant Human IL-1β: Comparison with Native Human IL-1β", *J. Immunol.* 138:1109 (1987).
Lomedico et al., "Cloning and Expression of Murine Interleukin-1 cDNA in *Escherichia Coli*", *Nature* 312:458 (1984).
Saklatvala et al., "Pig Interleukin 1", *J. Exp. Med.* 162:1208 (1985).

*Primary Examiner*—Ronald W. Griffin
*Assistant Examiner*—L. Eric Crane
*Attorney, Agent, or Firm*—Scott G. Hallquist; Christopher L. Wight

[57] ABSTRACT

Cloning and expression of nucleotide DNA segments encoding bovine IL-1β, and processes for producing purified bovine IL-1β as a product of recombinant cell culture, are disclosed.

6 Claims, 2 Drawing Sheets

FIGURE 1

```
   1 CGGGGCACAG CAAGCCACCC AGGGATCCTA TTCTCTCCAG CCAACCTTCA
  51 TTGCCCAGGT TTCTGAAACA GCCATGGCAA CCGTACCTGA ACCCATCAAC
 101 GAAATGATGG CTTACTACAG TGACGAGAAT GAGCTGTTAT TTGAGGCTGA
 151 TGACCCTAAA CAGATGAAGA GCTGCATCCA ACACCTGGAC CTCGGTTCCA
 201 TGGGAGATGG AAACATCCAG CTGCAGATTT CTCACCAGTT CTACAACAAA
 251 AGCTTCAGGC AGGTGGTGTC GGTCATCGTG GCCATGGAGA AGCTGAGGAA
 301 CAGTGCCTAC GCACATGTCT TCCATGATGA TGACCTGAGG AGCATCCTTT
 351 CATTCATCTT TGAAGAAGAG CCTGTCATCT TCGAAACGTC CTCCGACGAG
 401 TTTCTGTGTG ACGCACCCGT GCAGTCAATA AAGTGCAAAC TCCAGGACAG
 451 AGAGCAAAAA TCCCTGGTGC TGGCTAGCCC ATGTGTGCTG AAGGCTCTCC
 501 ACCTCCTCTC ACAGGAAATG AACCGAGAAG TGGTGTTCTG CATGAGCTTT
 551 GTGCAAGGAG AGGAAAGAGA CAACAAGATT CCTGTGGCCT TGGGTATCAA
 601 GGACAAGAAT CTATACCTGT CTTGTGTGAA AAAAGGTGAT ACGCCCACCC
 651 TGCAGCTGGA GGAAGTAGAC CCCAAAGTCT ACCCCAAGAG GAATATGGAA
 701 AAGCGCTTTG TCTTCTACAA GACAGAAATC AAGAATACAG TTGAATTTGA
 751 GTCTGTCCTG TACCCTAACT GGTACATCAG CACTTCTCAA ATCGAAGAAA
 801 GGCCCGTCTT CCTGGGACAT TTTGAGGTG GCCAGGATAT AACTGACTTC
 851 AGAATGGAAA CCCTCTCTCC CTAAAGAAAG CCATACCCAG GGAGTCCACG
 901 TGGGCTGAAT AACCCCGAGG ACTGGCAGAA GGGAAGGGAA GAATGTAGCT
 951 GCAGCCTGAA CTTCACTGTT GTCTGATCCA TGCCCGACTG CCTTCCCTGC
1001 ATTAGTGCTT AGAGATCTCC CCACGGCCAG GAGGAACAAT CCCCTCCTCC
1051 CAGAGCCCAT CCTCAGACCC CATCCACTGA GCCACCCCTC TCTCACTTCT
1101 ACTCACTCAA AGCCAGCCTG GCAAAACCA TGGCACACTA GTTTCAAAGA
1151 AATCCTCTGT CCTTTGCACC CAGCTTCTGA TGAGCAACCA CTTAACTATT
1201 TATTTATTTA TTTATTGATG TGTTAGTCTA TTTAATTTAG TTCCCAGGGG
1251 GCCTAGAAGC AGGCGCATCT GTGAAAAATC CTAGCCTTCA ATAACTGTGG
1301 AACCAATTTC CGGGTTAGAG TGCCATCCTT CTGTCAAGTC CTTTCACCAA
1351 GCCTGAAATA TACAAGCTCA GATTATTTAA ATAGAATTAT TTATAAATAG
1401 CGGAGAAGGC AATGGCACCC CACTCCAGTA CTCTTGCCTG GAAAATCCCA
1451 TGGATGGAGG AGCTTGGTAG GCTGCGGTCC ATGGGTCGC TAAGAGTCGG
1501 ACACGACTAG GCGACTTCAC TTTCACTTTT CACTTTCATG CATTGGAGAA
1551 GGAAATGGCA ACCTACTCCA GTGTTCTTGC CTGGAGAATC CCGGGGACGG
1601 GGGACCTGGT AGGCTACCGT CTATGGGGTC ACACAGAGTC GGACACGACT
1651 GAAGTGACTT AGCATAGCAT AGCATTTATG AATAGGGAAG AATGATCAGA
1701 TTGTTCAATG ATTTTGAAAT AAATTTCACT GAAAACAAAA AAAAAAAAA
```

FIGURE 2

```
ATG GCA ACC GTA CCT GAA CCC ATC AAC GAA ATG ATG GCT TAC TAC    45
Met Ala Thr Val Pro Glu Pro Ile Asp Glu Met Met Ala Tyr Tyr    15

AGT GAC GAG AAT GAG CTG TTA TTT GAG GCT GAT GAC CCT AAA CAG    90
Ser Asp Glu Asp Glu Leu Leu Phe Glu Ala Asp Asp Pro Lys Gln    30

ATG AAG AGC TGC ATC CAA CAC CTG GAC CTC GGT TCC ATG GGA GAT   135
Met Lys Ser Cys Ile Gln His Leu Asp Leu Gly Ser Met Gly Asp    45

GGA AAC ATC CAG CTG CAG ATT TCT CAC CAG TTC TAC AAC AAA AGC   180
Gly Asp Ile Gln Leu Gln Ile Ser His Gln Phe Tyr Asp Lys Ser    60

TTC AGG CAG GTG GTG TCG GTC ATC GTG GCC ATG GAG AAG CTG AGG   225
Phe Arg Gln Val Val Ser Val Ile Val Ala Met Glu Lys Leu Arg    75

AAC AGT GCC TAC GCA CAT GTC TTC CAT GAT GAT GAC CTG AGG AGC   270
Asp Ser Ala Tyr Ala His Val Phe His Asp Asp Asp Leu Arg Ser    90

ATC CTT TCA TTC ATC TTT GAA GAA GAG CCT GTC ATC TTC GAA ACG   315
Ile Leu Ser Phe Ile leu Glu Glu Glu Pro Val Ile Phe Glu Thr   105
                              ↓
TCC TCC GAC GAG TTT CTG TGT GAC GCA CCC GTG CAG TCA ATA AAG   360
Ser Ser Asp Glu Phe Val Cys Asp Ala Pro Val Gln Ser Ile Lys   120

TGC AAA CTC CAG GAC AGA GAG CAA AAA TCC CTG GTG CTG GCT AGC   405
Cys Lys Leu Gln Asp Arg Glu Gln Lys Ser Leu Val Leu Ala Ser   135

CCA TGT GTG CTG AAG GCT CTC CAC CTC CTC TCA CAG GAA ATG AAC   450
Pro Cys Val Leu Lys Ala Leu His Leu Leu Ser Asp Glu Met Asp   150

CGA GAA GTG GTG TTC TGC ATG AGC TTT GTG CAA GGA GAG GAA AGA   495
Arg Glu Val Val Phe Cys Met Ser Phe Val Gln Gly Glu Glu Arg   165

GAC AAC AAG ATT CCT GTG GCC TTG GGT ATC AAG GAC AAG AAT CTA   540
Asp Asp Lys Ile Pro Val Ala Leu Gly Ile Lys Asp Lys Asp Leu   180

TAC CTG TCT TGT GTG AAA AAA GGT GAT ACG CCC ACC CTG CAG CTG   585
Tyr Leu Ser Cys Val Lys Lys Gly Asp Thr Pro Thr Leu Gln Leu   195

GAG GAA GTA GAC CCC AAA GTC TAC CCC AAG AGG AAT ATG GAA AAG   630
Glu Glu Val Asp Pro Lys Val Tyr Pro Lys Arg Asp Met Glu Lys   210

CGC TTT GTC TTC TAC AAG ACA GAA ATC AAG AAT ACA GTT GAA TTT   675
Arg Phe Val Phe Tyr Lys Thr Glu Ile Lys Asp Thr Val Glu Phe   225

GAG TCT GTC CTG TAC CCT AAC TGG TAC ATC AGC ACT TCT CAA ATC   720
Glu Ser Val Leu Tyr Pro Asp Trp Tyr Ile Ser Ser Ser Gln Ile   240

GAA GAA AGG CCC GTC TTC CTG GGA CAT TTT CGA GGT GGC CAG GAT   765
Glu Glu Arg Pro Val Phe Leu Gly His Phe Arg Gly Gly Gln Asp   255

ATA ACT GAC TTC AGA ATG GAA ACC CTC TCT CCC TAA               798
Ile Thr Asp Phe Arg Met Glu Thr Leu Ser Pro End               266
```

BOVINE INTERLEUKIN-1β DNA SEQUENCE

BACKGROUND OF THE INVENTION

The present invention relates generally to mammalian cytokines, and particularly to cloning and expression of biologically active mammalian homologues of human IL-1β, e,g., bovine interleukin-1⊕. Interleukin-1 (IL-1) is the designation given to a family of polypeptides, released by macrophages and certain other cell types in response to immunogenic and traumatic stimulation, which have a primary role in initiating host response to injury and infection. These cytokines have been associated with a complex spectrum of biological activities. IL-1 is a primary immunostimulatory signal capable of inducing thymocyte proliferation via induction of interleukin-2 release, and of stimulating proliferation and maturation of B lymphocytes. In addition, IL-1 has been linked with prostaglandin production and induction of fever, and with promotion of wound healing. Reviews of the literature relating to IL-1 include Oppenheim et al., *Immunol. Today* 7: 45 (1986), and Durum el al., *Ann. Rev. Immunol.* 3: 263 (1985).

Human IL-1 activity resides in two distantly related proteins, which have been designated IL-1α and IL-1β (March et al., *Nature* 315: 641 (1985)). Both molecules are normally synthesized as larger precursors having molecular weights of about 30,000 daltons, which are subsequently processed by proteolytic cleavage to yield mature forms having molecular weights of approximately 17,500 daltons. While the precursor of human IL-1α exhibits IL-1 biological activity, the precursor of human IL-1β is biologically inactive, and must be cleaved to provide a mature version having IL-1 activity.

Recently, cDNAs coding for both human IL-1 species have been cloned and expressed in microorganisms, which has enabled production of sufficient quantities of IL-1α and IL-1β for preclinical research and potential therapeutic use.

In view of potential clinical utility as a vaccine adjuvant and component of wound-healing compositions, there is interest in employing bovine IL-1 proteins in veterinary medicine. Therapeutic compositions comprising biologically active quantities of bovine IL-1 proteins or active homologues could be employed to potentiate antibody production in response to vaccine antigens, and also to promote rapid epidermal wound-healing. An unexpected result of this invention is the observation that the specific activity of purified recombinant bovine IL-1β in stimulating bovine thymocyte proliferation is from three to four orders of magnitude greater than the specific activity of recombinant human IL-1β.

SUMMARY OF THE INVENTION

The present invention provides bovine IL-1β proteins, DNA segments encoding bovine IL-1β proteins, recombinant expression vectors comprising the DNA segments, microbial expression systems comprising the recombinant expression vectors, and processes for making the proteins using the microbial expression systems.

BRIEF DESCRIPTION OF THE DRAWINGS

FIG. 1 indicates the nucleotide sequence of a cDNA clone comprising the coding sequence of bovine IL-1β.

FIG. 2 depicts the nucleotide sequence and derived amino acid sequence of the coding region of the clone depicted in FIG. 1.

DETAILED DESCRIPTION OF THE INVENTION

A DNA segment encoding bovine IL-1β was isolated from a cDNA library prepared by reverse transcription of polyadenylated RNA isolated from bovine alveolar macrophages. A cDNA fragment corresponding to part of the coding sequence of human IL-1β was employed to screen the library by conventional DNA hybridization techniques. Clones which hybridized to the probe were analyzed by restriction endonuclease cleavage, agarose gel electrophoresis, and additional hybridization experiments ("Southern blots") involving the electrophoresed fragments. After isolating several clones which hybridized to the human cDNA probe, the hybridizing segment of one bIL-1β clone was subcloned and sequenced by conventional techniques. The coding sequence corresponding to the putative amino acid sequence of mature bIL-1β, determined by comparison to the corresponding native human sequence, was inserted into an appropriate expression vector and used to transform a suitable strain of *Esherichia coli*, which was then grown in culture under conditions favoring derepression of the recombinant transcriptional unit. The cultured cells were then harvested and cytosolic protein extracted and tested for interleukin-1 activity in bovine thymocyte proliferation and murine lymphocyte IL-2 production assays.

Definitions

"Bovine interleukin-1β" and "bIL-1β" refer to a bovine endogenous secretory protein whose biological properties include induction of bovine thymocyte proliferation via induction of IL-2 release, and stimulation of proliferation and maturation of bovine B-lymphocytes. The observed biological properties of the human homologue of bovine IL-1β also include induction of prostaglandin production and provision of a chemotactic signal to fibroblasts. As used throughout the specification, the term "mature bIL-1β" means a bIL-1β protein having bIL-1 biological activity and an amino acid sequence which is substantially homologous to the polypeptide sequence illustrated in FIG. 2, beginning with amino acid 114 and ending with amino acid 266. "Substantially homologous," which can refer both to nucleic acid and amino acid sequences, means that a particular subject sequence, for example, a mutant sequence, varies from a reference sequence by one or more substitutions, deletions, or additions, the net effect of which do not result in an adverse functional dissimilarity between reference and subject sequences. For purposes of the present invention, sequences having greater than 90 percent homology, equivalent biological activity, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents. "Mutant amino acid sequence" refers to a polypeptide encoded by a nucleotide sequence intentionally made variant from a native sequence. "Mutant protein" or "mutein" means a protein comprising a mutant amino acid sequence. "Native sequence" refers to an amino acid or nucleic acid sequence which is identical to a wild-type or native form of a gene or protein.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a bovine protein essentially free of native endogenous substances and unaccompanied by associated native glycosylation. Protein expressed in bacterial cultures will be free of polysaccharide; protein expressed in yeast will have a glycosylation pattern different from that expressed in mammalian cells.

"Purified", as used in the context of this disclosure, refers to bIL-1$\beta$ protein compositions having a specific activity in a bovine thymocyte mitogenesis assay of at least $1 \times 10^5$ units/mg. For purposes of the present invention, units of bIL-1$\beta$ activity are defined as the reciprocal dilution of a sample providing half-maximal proliferation-inducing activity, where one unit of activity is defined as that activity provided by a protein composition comprising purified recombinant human IL-1$\beta$ at a concentration of 100 $\mu$g/ml. Additional details regarding assay procedures are provided elsewhere in the specification.

"Substantially homogeneous bIL-1$\beta$" means a protein composition comprising purified bIL-1$\beta$, absent contaminating proteins in quantities detectable by conventional means, for example, staining of polyacrylamide gels. The efficiency of the microbial expression systems disclosed herein permits production of sufficient quantities of bovine IL-1$\beta$ to provide therapeutically useful quantities of substantially homogeneous material.

"DNA segment" refers to a DNA polymer, in the form of a separate fragment or as a component of a larger DNA construct, which has been derived from DNA isolated at least once in substantially pure form, i.e., in a quantity or concentration enabling identification, manipulation, and recovery of the segment and its component nucleotide sequences by standard biochemical methods, for example, using a cloning vector. "Nucleotide sequence" refers to a heteropolymer of deoxyribonucleotides. "Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Preferably, transcriptional units intended for use in yeast expression systems include a leader sequence enabling extracellular secretion of translated protein by a host cell. "Recombinant expression system" means a combination of an expression vector and a suitable host microorganism.

1. Assays for bIL-1$\beta$ Biological Activity a. Bovine Thymocyte Mitogenesis Assay Bovine IL-1$\beta$ activity can be monitored by a thymocyte mitogenesis assay, which involves ascertaining the capacity of a sample to induce proliferation of thymocytes from freshly killed calves. In this assay, approximately $1.5 \times 10^6$ Ficoll-Hypaque purified bovine thymocytes are dispensed into wells of a flat-bottom microtiter plate (Corning Plastics, Corning, NY, USA) in the presence of a submitogenic concentration of phytohemagglutinin-M (PHA-M) and serial three-fold serial dilutions of samples to be tested for bIL-1 activity.

Total culture volume per well is 200 microliters. Thymocytes are cultured in RPMI 1640 medium containing 50 U/ml penicillin, 50 $\mu$g/ml streptomycin, 2 mM glutamine, 0.2 mM gentamycin, 10 mM HEPES (N-2-hydroxyethylpiperazine-N'-2-ethanesulfonic acid) buffer, pH 7.4, $10^{-5}$M 2-mercaptoethanol, and 10% (v/v) fetal bovine serum. The samples are incubated for 68 hours at 37° C. in a humidified atmosphere of 5% $CO_2$ in air. Thereafter, cultures are pulsed for approximately 4 hours with 0.5 microcuries ($\mu$Ci) of tritiated thymidine ($^3$H-Tdr), incubated for an additional 4 hours, and then harvested onto glass fiber filter strips with the aid of a multiple-automated sample harvester. Details of this procedure are provided in U.S. Pat. No. 4,411,992.

In this assay, only cells cultured in the presence of IL-1 incorporate $^3$H-Tdr in a dose-dependent manner. Bovine thymoctyes cultured in the absence of IL-1 incorporate only background levels of radiolabel. IL-1 activity is calculated from the linear portion of the $^3$H-Tdr incorporation data. Units of IL-1 activity are determined as the reciprocal dilution of a sample which generates 50% of maximal thymocyte $^3$H-Tdr incorporation, where one unit of activity is provided by a standard solution comprising purified recombinant human IL-1$\beta$ at a concentration of 100 $\mu$g/ml.

b. IL-1 Conversion Assay

Alternatively, IL-1 activity can be assayed by an IL-1 conversion assay, which is based upon the observation that bIL-1 induces certain IL-1-dependent-IL-2-producing cell lines, for example, the murine T-cell line LBRM-33-1A5 (ATCC CRL-8079) to produce IL-2. IL-1 conversion assays are described by Conlon, *J. Immunol.* 131: 1280 (1983) and Lowenthal el al., *J. Immunol.* 137: 1226 (1986). In these assays, cells to be induced are first inactivated by treatment with 50 $\mu$g/ml mitomycin-C and then incubated in the presence of a suboptimal mitogenic concentration of PHA-M, varying dilutions of sample, and IL-2 dependent cells, for example the murine T-cell line CTLL-2 (ATCC TIB 214). Only the IL-2 dependent cells added to wells previously contacted with IL-1 (thereby inducing IL-2 production by the inactivated cells) will proliferate and incorporate radiolabel. Conversion assays of this type are both more rapid and more sensitive than the thymocyte mitogenesis assay.

In a preferred conversion assay, approximately $5 \times 10^4$ inactivated EL4-6.1 cells are dispensed into wells of a flat-bottom microtiter plate containing serial threefold dilutions of samples to be tested for activity. Cells are cultured in a total volume of 100 microliters of complete Clicks medium containing 50 U/ml penicillin, 50 $\mu$g/ml streptomycin, 2 mM glutamine, 0.2 mM gentamycin, 10 mM HEPES buffer, pH 7.4, $10^{-5}$M 2-mercaptoethanol, and 10% (v/v) fetal bovine serum. The samples are incubated for 24 hours at 37° C. in a humidified atmosphere of 5% $CO_2$ in air. At this point, approximately $4 \times 10^3$ washed CTLL-2 cells are added and incubation continued for an additional 20 hours. Finally, cultures are pulsed for approximately 4 hours with 0.5 microcuries ($\mu$Ci) of tritiated thymidine ($^3$H-Tdr), incubated for an additional 4 hours, and the resulting pulsed cultures assayed for thymidine incorporation as detailed above.

Protein and Endotoxin Assays

Protein concentrations can be determined by any suitable method. However, the Bio-Rad total protein assay (Bio-Rad Laboratories, Richmond, Calif., USA) is preferred. SDS-PAGE can also be employed to monitor purification progress, substantially as described by Kronheim et al., *J. Exp. Med.* 161: 490 (1985), or other suitable techniques. Additional details regarding use of variants of the IL-1 assays described above are disclosed by Conlon, *J. Immunol.* 131: 1280 (1983) and Kronheim et al., supra.

Endotoxin levels in protein compositions are conveniently assayed using a commercial kit available from Whittaker Bioproducts, Walkersville, Md., U.S.A., (Quantitative Chromogenic LAL QCL-1000) or its equivalent. This method uses a modified Limulus amebocyte lysate and synthetic color-producing substrate to detect endotoxin chromogenically. Purified recombinant bIL-1$\beta$ is tested for presence of endotoxin at multiple dilutions. The assay is preferably performed shortly following completion of purification and prior to storage at $-70°$ C. To minimize the possibility of bacterial contamination during the purification process itself, sterile buffers should be employed.

The Native bIL-1$\beta$ Sequence

The nucleotide sequence of a cDNA clone isolated from a bovine alveolar macrophage library is set forth in FIG. 1. The initiator methionine (at nucleotide 74), first codon of mature bIL-1$\beta$ (at nucleotide 413) and stop codon (at nucleotide 874) are underlined.

FIG. 2 indicates the cDNA and deduced amino acid sequences of the coding region of the bIL-1$\beta$ clone fully set forth in FIG. 1. As in the case of human IL-1$\beta$, bIL-1$\beta$ is apparently translated in vivo as an inactive precursor protein of approximately 32,000 dalton molecular weight, which is subsequently processed by an endogenous protease or proteases to provide the mature form, which has a predicted molecular weight of about 18,000 daltons. In FIG. 2, nucleotides and amino acids are numbered beginning with the initiator methionine of the precursor. The mature sequence, which is underlined, begins with a GCA codon specifying the alanine residue indicated by an arrow at residue 114.

A recombinant DNA segment encoding the amino acid sequence of bIL-1$\beta$ can be obtained by screening of appropriate cDNA libraries using appropriate probes, or by assembly of artificially synthesized oligonucleotides. Using similar techniques, cDNAs encoding other mammalian homologues of human IL-1$\beta$ can be isolated and used to construct expression vectors.

Construction of Expression Vectors

Mature bIL-1$\beta$ can be expressed in bacteria, yeast, mammalian, or other cells under the control of appropriate inducible promoters.

Appropriate expression vectors for bacterial use are constructed by inserting the heterologous structural DNA sequence encoding bIL-1$\beta$ together with translational initiation and termination signals in operable reading phase with a functional promoter. The vector will comprise one or more phenotypic selectable markers and an origin of replication to ensure amplification within the host. Optionally, the heterologous sequence can be integrated into the vector such that it is translated as a fusion protein, in conjunction with an identification peptide (e.g., DYKDDDDK) or other sequence imparting desired characteristics relating to stabilization or purification of expressed protein. As a representative, but nonlimiting example, useful expression vectors for bacterial use can comprise a selectable marker and bacterial origin of replication derived from commercially available plasmids comprising sequences derived from the well known cloning vector pBR322 (ATCC 37017). Such commercial vectors include, for example, pKK223-3 (Pharmacia Fine Chemicals, Uppsala, Sweden) and pGEM1 (Promega Biotec, Madison, WI, USA). These "backbone" sections are combined with an appropriate promoter and the structural sequence to be expressed.

A particularly useful bacterial expression system employs the phage $\lambda$ PL promoter and cI857ts thermolabile repressor. Plasmid vectors available from the American Type Culture Collection which incorporate derivatives of the $\lambda$ P$_L$ promoter include plasmid pHUB2, resident in *E. coli* strain JMB9 (ATCC 37092) and pPLc28, resident in *E. coli* RR1 (ATCC 53082). Other useful promoters for expression in *E. coli* include the T7 RNA polymerase promoter described by Studier et al., *J. Mol. Biol.* 189: 113 (1986), the lac promoter described by Lauer, *J. Mol. Appl. Genet.* 1: 139–147 (1981) and available as ATCC 37121, and the tac promoter described by Maniatis, *Molecular Cloning: A Laboratory Manual* (Cold Spring Harbor Laboratory, 1982, p 412) and available as ATCC 37138.

Following transformation of a suitable host strain and growth of the host strain to an appropriate cell density, the selected promoter is depressed by appropriate means (e.g., temperature shift or chemical induction) and cells cultured for an additional period. Cells are typically harvested by centrifugation, disrupted by physical or chemical means, and the resulting crude extract retained for further purification.

Yeast systems may also be used for expression of the recombinant proteins of this invention. Generally, useful yeast vectors will include origins of replication and selectable markers permitting transformation of both yeast and *E. coli*, e.g., the ampicillin resistance gene of *E. coli* and yeast TRP1 gene, and a promoter derived from a highly-expressed yeast gene to induce transcription of a downstream structural sequence. The heterologous structural sequence is assembled in appropriate phase with translation initiation and termination sequences, and preferably, a leader sequence causing secretion of translated protein into the extracellular medium.

Useful yeast vectors can be assembled using DNA sequences from pBR322 for selection and replication in *E. coli* (Ap$^r$ gene and origin of replication) and yeast DNA sequences including a glucose-repressible alcohol dehydrogenase 2 (AHD2) promoter. The ADH2 promoter has been described by Russell et al., *J. Biol. Chem.* 258: 2674 (1982) and Beier et al., *Nature* 300: 724 (1982). Such vectors may also include a yeast TRP1 gene as a selectable marker and the yeast 2$\mu$ origin of replication. The yeast $\alpha$-factor leader sequence, enabling secretion of heterologous proteins from a yeast host, can be inserted adjacent to the promoter and translation initiation sequence and in phase with the structural gene to be expressed. The $\alpha$-factor leader sequence may be modified to contain, near its 3' end, one or more useful restriction sites to facilitate fusion of the leader sequence to foreign genes. Alternative expression vectors are yeast vectors which comprise other promoters, for example, the yeast $\alpha$-factor promoter or 3-phosphoglycerate kinase (PGK) promoter.

Suitable yeast transformation protocols are known to those skilled in the art; and an exemplary technique is described by Hinnen, et al., *Proc. Natl. Acad. Sci. USA* 75: 1929 (1978), selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 or α-factor promoters are grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and frozen or held at 4° C. prior to further purification.

Various mammalian cell culture systems can also be employed to express recombinant protein. Examples of mammalian expression systems include the COS-7 lines of monkey kidney fibroblasts, described by Gluzman, *Cell* 23: 175 (1981), and other cell lines capable of expressing a compatible vector, for example, the C127, 3T3, CHO, HeLa and BHK cell lines. Mammalian expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Microbial Expression and Protein Purification

The general purification scheme described herein involves an initial acid extraction from cell pellets, followed by ion exchange chromatography in aqueous media. The ion exchange chromatography may comprise cation exchange chromatography followed by anion exchange chromatography.

Suitable cation exchange chromatography media include various insoluble matrices comprising sulfopropyl or carboxymethyl groups. Sulfopropyl groups are preferred. The matrices can be acrylamide, agarose, dextran, cellulose or other ion exchange resins or substrates commonly employed in protein purification. A particularly useful material for cation exchange chromatography of recombinant bIL-1β (rbIL-1β) is Sulphopropyl Sephadex (SPS) C-25 (Pharmacia Fine Chemicals, Uppsala, Sweden). When media containing sulfopropyl groups are employed, extracts containing rbIL-1β species are applied at a pH of about 4.0, in a suitable buffer such as sodium citrate. rbIL-1β is bound by the ion exchanger, and can be eluted by application of a weakly basic eluant, for example, 10 mM Tris-HCl, pH 8.1.

Suitable anion exchange chromatography media include various insoluble matrices comprising diethylaminoethyl (DEAE) or diethyl-(2-hydroxypropyl)aminoethyl (QAE) groups. DEAE groups are preferred. The matrices can be acrylamide, agarose, dextran, cellulose or other types commonly employed in protein purification. A useful material for cation exchange chromatography of rbIL-1β is DEAE-Sephacel (Pharmacia). When media containing DEAE groups are employed, extracts containing rbIL-1β are applied at a weakly basic pH. For example, pooled rbIL-1β-containing fractions resulting from a previous cation exchange chromatography step (at a pH of about 8.1) can be applied directly in a suitable buffer such as Tris-HCl. rbIL-1β has been observed to elute (in wash fractions) unbound by DEAE Sephacel, while substantially all *E. coli* protein contaminants, including pyrogens, were bound.

Experiments in which the pH of the initial extraction buffer was varied have indicated that extraction of rbIL-1β from *E. coli* is optimally performed under acid conditions, for example, pH 3.5–4.4, preferably about pH 4.0, in order to precipitate unwanted proteins while solubilizing rbIL-1β. The optimal pH for the initial extraction step may vary between fermenter batches. For this reason, small-scale pilot runs may be employed to determine optimal pH, particularly where large quantities of material are involved.

As noted previously, rbIL-1β can be efficiently produced by growth and derepression of appropriate *E. coli* cells harboring high level thermoinducible expression plasmids. Cells are grown, for example, in a 10 liter fermenter employing conditions of maximum aeration and vigorous agitation. An antifoaming agent (Antifoam A) is preferably employed. Cultures are grown at 30° C. in the superinduction medium disclosed by Mott et al., *Proc. Natl. Acad. Sci. USA* 82: 88 (1985), optionally including antibiotics, derepressed at a cell density corresponding to $A_{600}=0.4$–$0.5$ by elevating the temperature to 42° C., and harvested 16 hours after the upward temperature shift. The cell mass is initially concentrated by filtration or other means, then centrifuged at $10,000\times g$ for 10 minutes at 4° C. followed by rapid freezing of the cell pellet.

To achieve the initial acid extraction, cell pellets are suspended in 30 mM Tris-HCl buffer, pH 8, containing 5 mM EDTA and 1 mM phenylmethylsulfonyl fluoride (PMSF). The resulting suspension is rapidly frozen in a dry ice/methanol bath and then thawed. Next, 30 mM sodium citrate buffer at pH 4.0, containing 5 mM EDTA and 250 μg/ml lysozyme is added to the suspensions. In larger runs, cells can be disrupted in pH 4.0 buffers using a cell homogenizer. The resulting acid suspensions are incubated for 60 minutes in a 37° C. water bath. Following incubation, the extracts are rapidly frozen in a dry-ice/methanol bath, thawed, and then centrifuged at 4° C. for 45 minutes at $38,000\times g$. Supernatants are then decanted for use in the next purification step.

Extraction of rbIL-1β from *E. coli* cell suspensions at pH 4.0 results in precipitation of most contaminating proteins and significant recovery of rbIL-1β activity. Extracts containing rbIL-1β can be applied at pH 4.0 to an SPS C-25 column pretreated with 0.1% Triton X-100 (polyoxyethylene ether; Sigma Chemical Company, St. Louis, Mo., USA) and 10% fetal calf serum. The column can then be washed with 3 column volumes of 10 mM 2-(N-morpholino)ethanesulfonic acid (MES) buffer, pH 5.0, and protein eluted from the column with 10 mM Tris-HCl, pH 8.1.

Fractions containing bIL-1 activity from the SPS step can then be combined and applied to columns containing DEAE-Sephacel previously equilibrated with 10 mM Tris-HCl pH 8.1. The DEAE columns are washed with additional starting buffer to elute bIL-1β which is substantially pure by SDS-PAGE.

The forgoing ion exchange chromatography procedures can be repeated to attain further purification, or combined with subsequent size exclusion chromatography or high-performance liquid chromatography (HPLC) steps to attain a final product of high purity.

Administration of IL-1

In use, purified bovine IL-1β is administered to a mammal for treatment in a manner appropriate to the indication. Thus, for example, bIL-1β administered as a vaccine adjuvant will be given in conjunction with or shortly following administration of an appropriate vaccine antigen. Administration may be by injection, continuous infusion, sustained release from implants, or other suitable technique. Where bIL-1β is administered as an aid to wound healing, it will typically be applied topically to the site of injury, for example, in conjunction with a wound dressing. Therapeutically-effective dosage levels are determined by initiating treatment at higher dosage levels and reducing the amounts of bIL-1β administered until wound healing is no longer achieved. Generally, therapeutic dosages will range from about 0.1 to 1000 ng rbIL-1β per kg body weight, preferably 1-100 ng/kg. Typically, bIL-1β will be administered in the form of a composition comprising purified protein in conjunction with physiologically acceptable carriers, excipients or diluents. Neutral buffered saline or saline mixed with conspecific serum albumin are exemplary appropriate diluents.

EXAMPLE: ISOLATION OF cDNA ENCODING bIL-1β AND MICROBIAL EXPRESSION OF ACTIVE PROTEIN

A cDNA polynucleotide probe was prepared from a 570 base pair (bp) SstI-PvuII fragment of the structural sequence of a human IL-1β cDNA by nick-translation using DNA polymerase I. The method employed was substantially similar to that disclosed by Maniatis et al., supra, p. 109.

A cDNA library was constructed by reverse transcription of polyadenylated mRNA isolated from total RNA extracted from bovine alveolar macrophages (BAM). BAM were cultured in RPMI 1640 medium plus 10% fetal bovine serum for 16 hours with 10 μg/ml *Salmonella typhimurium* lipopolysaccharide (LPS) in order to elicit maximal IL-1 specific messenger RNA production. The cDNA was rendered double-stranded using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., *DNA Cloning: A Practical Approach*, Glover, ed., IRL Press, pp. 49–78). The ligated DNA was packaged into phage particles using a commercially available kit to generate a library of recombinants (Stratagene Cloning Systems, San Diego, CA, USA 92121). 50,000–200,000 recombinants were plated on *E. coli* strain C600(hfl⁻) and screened by standard plaque hybridization techniques under conditions of moderate stringency (60° C., 6xSSC). Ten clones were isolated from the library which hybridized to the cDNA probe.

The clones were plaque purified and used to prepare bacteriophage DNA which was digested with EcoRI. The digests were electrophoresed on an agarose gel, blotted onto nylon filters, and retested for hybridization. The clones were digested with EcoRI followed by preparative agarose gel electrophoresis, then subcloned into an EcoRI-cut derivative (pGEMBL) of the standard cloning vector pBR322 containing a polylinker having a unique EcoRI site, a BamH1 site and numerous other unique restriction sites. An exemplary vector of this type is described by Dente et al., *Nucleic Acids Research* 11: 1645 (1983). Restriction mapping indicated the presence of an insert of approximately 1.8 kilobases (kb) in two of the clones. These were subcloned and sequenced. Clone bovIL-1β9.3 included a DNA segment encoding a protein of 266 amino acids having a predicted molecular weight of 31 kilodaltons (Kd) and bearing approximately 62% homology to human IL-1β. In vitro transcription and translation of this clone in a rabbit reticulocyte lysate system resulted in synthesis of IL-1β protein of approximately 31 Kd.

A bacterial expression vector was constructed by digesting the cloning vector including the bIL-1β sequence with NheI and BglII, and isolating the resulting 540 bp fragment encoding mature bIL-1β. This fragment was then ligated to the following oligonucleotide polylinker:

| ClaI | | | | | | | | | | | | | | |
|---|---|---|---|---|---|---|---|---|---|---|---|---|---|---|
| C | GAT | ACT | ATG | GCA | CCT | GTT | CAA | TCA | ATA | AAA | TGT | AAG | CTT | CAA | GAT |
|  | TA | TGA | TAC | CGT | GGA | CAA | GTT | AGT | TAT | TTT | ACA | TTC | GAA | GTT | CTA |
|  |  |  | Met | Ala | Pro | Val | Gln | Ser | Ile | Lys | Cys | Lys | Leu | Gln | Asp |
|  |  |  |  |  |  |  |  |  | NheI |  |  |  |  |  |  |
|  | AGA | GAA | CAA | AAA | TCT | CTG | GTT | CTG | G |  |  |  |  |  |  |
|  | TCT | CTT | GTT | TTT | AGA | GTC | CAA | GAC | CGA | TC |  |  |  |  |  |
|  | Arg | Glu | Gln | Lys | Ser | Leu | Val | Leu | Ala | Ser |  |  |  |  |  |

The resulting construct was ligated into ClaI- and BamHI-cut pPL3 for thermoinducible expression in *E. coli* K802 (pRK248cIts; ATCC 33526). pPL3 is a derivative of pBR322 comprising a version of the phage λ $P_L$ promoter previously described. Assay of a crude SDS extract of bacteria comprising the bIL-1β expression vector, grown under conditions favoring expression, indicated significant biological activity in the bovine thymocyte proliferation assay.

The K802 strain transformed with the foregoing expression vector were grown in 500 ml shake-flask culture to an $OD_{600}$ of 0.4–05, depressed by raising culture temperature to 42° C., and grown an additional three hours prior to harvest. At harvest, the culture $OD_{600}$ was about 1.6. The bacteria were harvested by centrifugation and the pellet frozen at −80° C. The frozen pellet was thawed, disrupted, and rbIL-1β solubilized by acid extraction at pH 4.0. The supernatant was applied and eluted from SPS-Sephadex and DEAE-Sephacel substantially as previously described. rbIL-1β eluted unbound from the DEAE-Sephacel, substantially free of contaminating proteins as indicated by SDS-PAGE. A sample of the purified rbIL-1β was assayed using the bovine thymoctye proliferation assay, employing 0.3% PHA-M as the submitogenic stimulus. A sample comprising 36 μg/ml purified rbIL-1β exhibited approximately 9000 units of activity, relative to 1 unit provided by a 100 μg/ml standard of recombinant human IL-1β. Thus, the rbIL-1β in the sample exhibited a specific activity of about 250,000 units (as defined) per mg.

What is claimed is:

1. An isolated DNA segment encoding bovine interleukin-1β (bIL-1β).

2. An isolated DNA segment having a nucleotide sequence encoding the following amino acid sequence:

Ala Pro Val Gln Ser Ile Lys Cys Lys Leu Gln Asp Arg Glu Gln

Lys Ser Leu Val Leu Ala Ser Pro Cys Val Leu Lys Ala Leu His

Leu Leu Ser Asp Glu Met Asp Arg Glu Val Val Phe Cys Met

Ser Phe Val Gln Gly Glu Glu Arg Asp Asp Lys Ile Pro Val

Ala Leu Gly Ile Lys Asp Lys Asp Leu Tyr Leu Ser Cys Val

Lys Lys Gly Asp Thr Pro Thr Leu Gln Leu Glu Glu Val Asp

Pro Lys Val Tyr Pro Lys Arg Asp Met Glu Lys Arg Phe Val

Phe Tyr Lys Thr Glu Ile Lys Asp Thr Val Glu Phe Glu Ser

Val Leu Tyr Pro Asp Trp Tyr Ile Ser Ser Ser Gln Ile Glu

Glu Arg Pro Val Phe Leu Gly His Phe Arg Gly Gly Gln Asp

Ile Thr Asp Phe Arg Met Glu Thr Leu Ser Pro

3. An isolated DNA segment having the following sequence of nucleotides:

GCA CCC GTG CAG TCA ATA AAG TGC AAA CTC CAG

GAC AGA GAG CAA AAA TCC CTG GTG CTG GCT AGC

CCA TGT GTG CTG AAG GCT CTC CAC CTC CTC TCA

CAG GAA ATG AAC CGA GAA GTG GTG TTC TGC ATG

AGC TTT GTG CAA GGA GAG GAA AGA GAC AAC

AAG ATT CCT GTG GCC TTG GGT ATC AAG GAC AAG

AAT CTA TAC CTG TCT TGT GTG AAA AAA GGT GAT

ACG CCC ACC CTG CAG CTG GAG GAA GTA GAC CCC

AAA GTC TAC CCC AAG AGG AAT ATG GAA AAG

CGC TTT GTC TTC TAC AAG ACA GAA ATC AAG AAT

ACA GTT GAA TTT GAG TCT GTC CTG TAC CCT AAC

TGG TAC ATC AGC ACT TCT CAA ATC GAA GAA AGG

CCC GTC TTC CTG GGA CAT TTT CGA GGT GGC CAG

GAT ATA ACT GAC TTC AGA ATG GAA ACC CTC TCT

CCC

4. A recombinant expression vector comprising a DNA segment according to claim 1.

5. A recombinant expression vector comprising a DNA segment according to claim 2.

6. A recombinant expression vector comprising a DNA segment according to claim 3.

* * * * *